United States Patent [19]
Schmitt

[11] Patent Number: 5,509,931
[45] Date of Patent: Apr. 23, 1996

[54] RAVEL-RESISTANT SELF-SUPPORTING WOVEN VASCULAR GRAFT

[75] Inventor: Peter J. Schmitt, Garnerville, N.Y.

[73] Assignee: Meadox Medicals, Inc., Oakland, N.J.

[21] Appl. No.: 188,560

[22] Filed: Jan. 28, 1994

Related U.S. Application Data

[60] Continuation of Ser. No. 875,876, Apr. 29, 1992, Pat. No. 5,282,846, which is a division of Ser. No. 573,947, Aug. 28, 1990, abandoned.

[51] Int. Cl.$^6$ .................................................... A61F 2/06
[52] U.S. Cl. .................................................. 623/1; 623/12
[58] Field of Search .................................... 623/1, 11, 12; 606/194, 198, 153; 600/36; 604/8

[56] References Cited

U.S. PATENT DOCUMENTS

| | | |
|---|---|---|
| 2,836,181 | 5/1958 | Tapp . |
| 3,096,560 | 7/1963 | Liebig et al. . |
| 3,272,204 | 9/1966 | Artandi et al. . |
| 3,304,557 | 2/1967 | Polansky . |
| 3,316,610 | 5/1967 | Manock . |
| 3,479,245 | 11/1969 | Manock . |
| 3,479,670 | 11/1969 | Medell . |
| 3,853,462 | 12/1974 | Smith . |
| 3,878,565 | 4/1975 | Sauvage . |
| 3,945,052 | 3/1976 | Liebig . |
| 3,953,566 | 4/1976 | Gore . |
| 3,986,828 | 10/1976 | Hoffman, Jr. et al. . |
| 4,047,252 | 9/1977 | Liebig et al. . |
| 4,126,499 | 11/1978 | Payen . |
| 4,187,390 | 2/1980 | Gore . |
| 4,191,218 | 3/1980 | Clark . |
| 4,192,020 | 3/1980 | Davis . |
| 4,306,318 | 12/1981 | Mano et al. . |
| 4,340,091 | 7/1982 | Skelton . |
| 4,517,687 | 5/1985 | Liebig et al. . |
| 4,530,113 | 7/1985 | Matterson . |
| 4,632,842 | 12/1986 | Karwoski et al. . |
| 4,652,263 | 3/1987 | Herweck et al. . |
| 4,718,907 | 1/1988 | Karwoski et al. . |
| 4,892,539 | 1/1990 | Koch . |

FOREIGN PATENT DOCUMENTS

| | | |
|---|---|---|
| 0122744 | 10/1984 | European Pat. Off. . |
| 2522696 | 9/1983 | France . |
| 770678 | 3/1957 | United Kingdom . |
| 820014 | 6/1959 | United Kingdom . |
| 1563450 | 3/1980 | United Kingdom . |
| 8303752 | 11/1983 | WIPO . |
| 8705796 | 10/1987 | WIPO . |
| 8905371 | 6/1989 | WIPO . |

*Primary Examiner*—Debra S. Brittingham
*Attorney, Agent, or Firm*—Hoffmann & Baron

[57] ABSTRACT

A ravel-resistant, self-supporting woven synthetic fabric vascular graft including a fusible fiber integrated into the weave in the filling yarn is provided. The graft is woven from multifilament polyester warp yarns which can be textured or flat. The filling yarn includes a low melting fusible fiber or resin which can be combined with a stiff monofilament. The monofilament component provides radial rigidity to improve kink and crush resistance. After heat setting, the low melting fusible resin fuses to orthogonal warp yarns at each intersection and provides ravel resistance to the finished graft. Improved kink resistance make the tubular grafts suitable for use in medium and small diameter peripheral applications. A preferred graft has a single velour outer surface and a smooth inner surface.

27 Claims, 1 Drawing Sheet

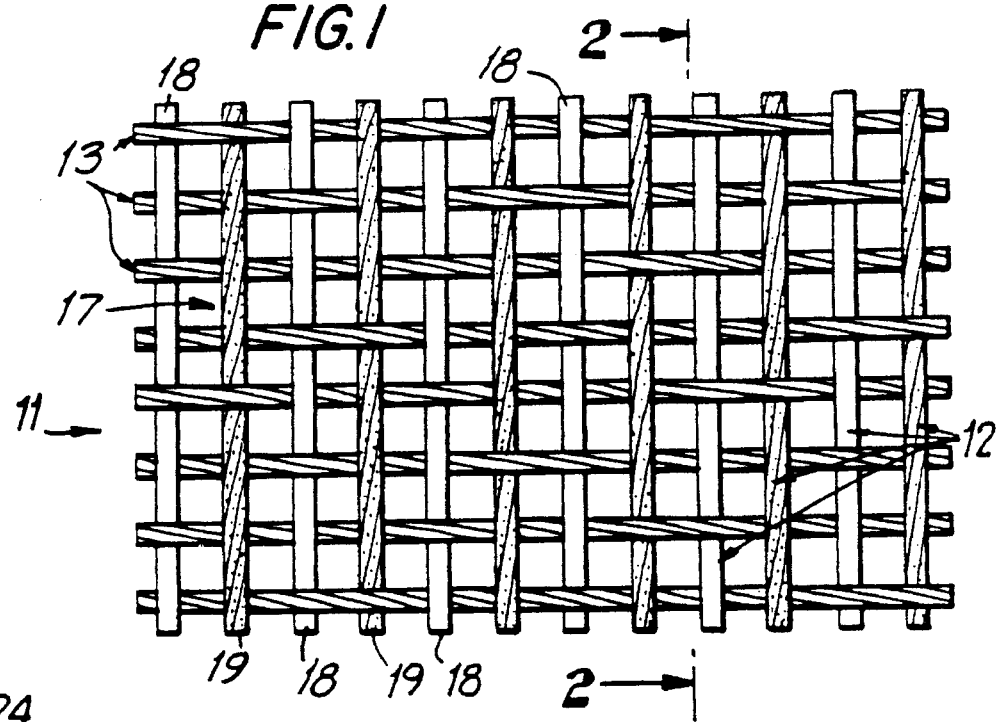
FIG. 1
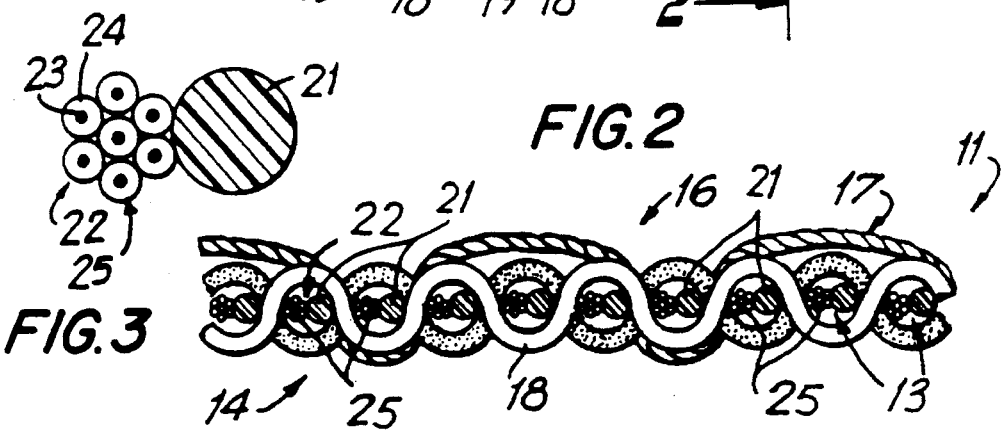
FIG. 2
FIG. 3
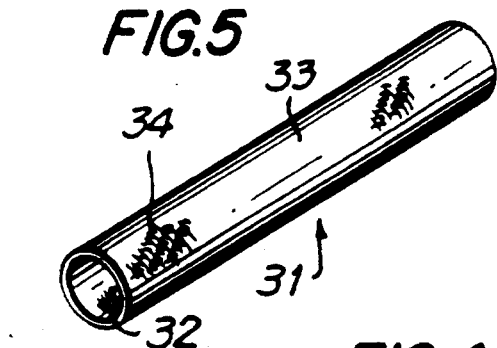
FIG. 5
FIG. 4
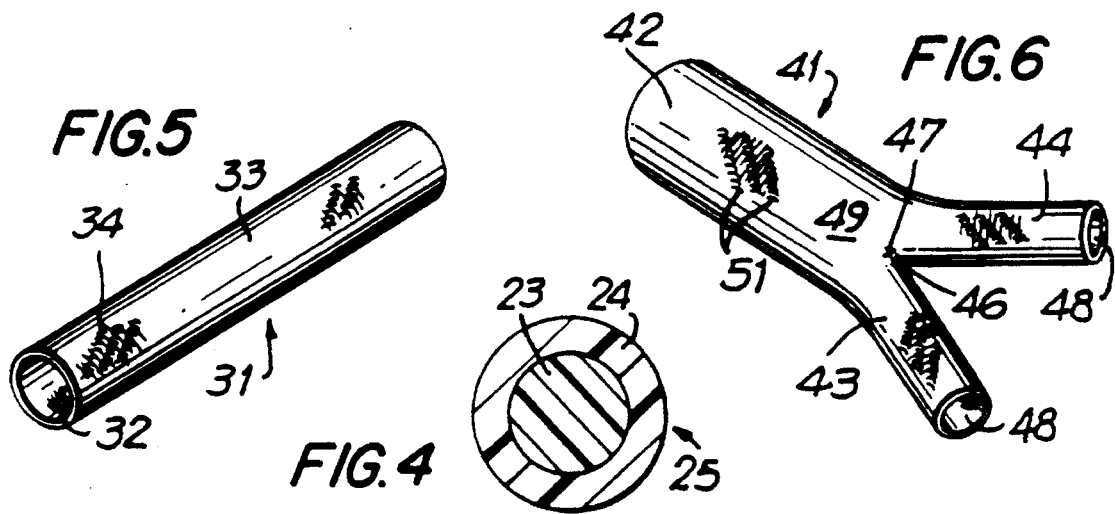
FIG. 6

RAVEL-RESISTANT SELF-SUPPORTING WOVEN VASCULAR GRAFT

This is a continuation of application Ser. No. 07/875,876 filed Apr. 29, 1992, now U.S. Pat. No. 5,282,846 issued on Feb. 1, 1994 which is a divisional of application Ser. No. 07/573,947 filed on Aug. 28, 1990, and now abandoned.

BACKGROUND OF THE INVENTION

This invention relates to synthetic vascular grafts, and more particularly to synthetic woven vascular grafts which are ravel-resistant due to inclusion of a fusible component and self-supporting due to inclusion of a stiffening component.

Vascular grafts of synthetic materials are widely used for the replacement of segments of human blood vessels. Synthetic vascular grafts have taken a wide variety of configurations and are formed of a wide variety of materials. Among the accepted and successful vascular graft implants are those formed from a biologically compatible material in tubular form which retain an open lumen to permit blood to flow normally through the graft after implantation. The biologically compatible materials include thermoplastic materials such as polyester, polytetrafluoroethylene (PTFE), silicone and polyurethanes. The most widely used are polyester fibers and PTFE. The polyester fibers, usually Dacron, may be knit or woven and may be of a monofilament, or multifilament, or staple yarn, or combination of each.

There are a wide variety of synthetic vascular grafts presently in use. An important factor in the selection of a particular graft is the porosity of the substrate of which the graft is formed and the strength requirements for the implant. Porosity is significant, because it controls the tendency to hemorrhage during and after implantation and influences ingrowth of tissue into the wall of the graft.

Synthetic fabric vascular grafts may be of a woven, knit or velour construction. A synthetic vascular graft having a warp-knit construction is disclosed by William J. Liebig in U.S. Pat. No. 3,945,052. Another graft having a warp knit double-velour construction is described by Liebig and German Rodriquez in U.S. Pat. No. 4,047,252. William J. Liebig and Dennis Cummings describe a synthetic woven double-velour graft in U.S. Pat. No. 4,517,687; the velour loops being formed of warp yarns which are texturized preshrunk multifilament yarns. These three issued United States patents for synthetic vascular grafts are assigned to the assignee of this application.

U.S. Pat. No. 4,892,539 issued to Durmus Koch describes a synthetic fabric woven graft with a single velour on the outer surface. The graft is described as woven from multifilament polyester yarns, specifically described as texturized, with the single outer velour formed of filling yarns with each velour loop extending outside a plurality of warp yarns.

After knitting or weaving the yarns into a tubular graft, the graft is compacted by a method such as disclosed in U.S. Pat. No. 3,853,462 to Ray E. Smith and No. 3,986,828 to Harmon Hoffman and Jacob Tolsma also assigned to the same assignee as this application. Compaction results in shrinking of the yarns in the fabric and generally reduces the overall porosity of the fabric substrate. These tubular grafts after compacting generally have a diameter from about 6 mm to 40 mm.

Subsequent to compacting, synthetic tubular fabric grafts are crimped. Crimping involves forming ridges in the wall of the grafts to eliminate the danger of kinking or collapse of the tubing when flexed and results in uniform, regular, circular corrugations which provide uniform strength over the entire surface of the graft tubing. This applies to both the woven and knit fabric vascular grafts. Examples are shown by L. R. Sauvage in U.S. Pat. No. 3,878,565 who describes a tubular textile synthetic fiber prosthesis of a body having a multiplicity of outwardly extending fiber loops. In FIG. 2a, the graft body is crimped into irregular, circumferential corrugations. The degree of protection afforded by irregular corrugation varies over the lengths of the tube and can fall below the required level of protection at specific regions. The warp-knit and woven grafts described above in U.S. Pat. No. 3,945,052, No. 4,047,252 and No. 4,517,687 are circularly crimped. The graft in U.S. Pat. No. 4,892,539 is crimped in a spiral fashion. Crimped or corrugated walls can disrupt blood flow and create areas of thick tissue buildup, due to the profile.

S. Polansky in U.S. Pat. No. 3,304,557 avoids crimping in vascular prothesis by forming a tube with repeating reinforcing ring sections. These reinforcing ring sections incorporate reinforcing picks adjacent only the outer surface. He proposes that the annular rings can be in the form of a helix, alternating rings and helix-loops. These latter suggestions are similar to the tubular prosthesis of I. B. Medell in U.S. Pat. No. 3,479,670 wherein an open mesh tube is wrapped with two polypropylene monofilament right-hand and left-hand helices and fused to penetrate partially the exterior of the tube. In U.S. Pat. No. 3,272,204 to C. Artandi and L. D. Bechtol sew a Dacron fabric to Teflon rings or a helix to prevent an absorbable collagen reinforced graft tube from collapsing.

Selection of a particular type of graft substrate by a vascular surgeon depends upon several factors. Among the factors included is the particular location of the implantation. This also dictates the size of the graft in order to maintain a sufficiently large or small lumen to accommodate the normal blood flow in the region of implantation. The ultimate strength requirements and blood pressure in the location of implantation also affects the selection. Generally, the woven grafts provide greater strength and reduced porosity, but are generally considered to be more difficult to handle and suture and tend to unravel when cut, particularly at an oblique angle. Velours are often preferred because the velour surfaces facilitate growth of tissue into the loops extending from the surface of the velour fabric. The knitted grafts are generally softer and more easily sutured, but are generally more porous. Depending on the location of the implant and heparinization condition of the patient, synthetic fabric grafts generally must be preclotted with the patients blood before implantation. Preclotting may not be essential with a woven graft, but is generally recommended nonetheless.

Tubular grafts of smaller diameter, for example, 6 mm and below are often utilized in peripheral regions of the body and appendages. Today, the most successful in this respect are grafts of PTFE of the material disclosed by Robert W. Gore in U.S. Pat. No. 4,187,390 and No. 3,953,566. These grafts are formed by extrusion of the PTFE material. While accepted for use in small diameter applications, PTFE grafts often require surgical replacement within relatively short periods of time compared to the larger diameter fabric vascular grafts described above, Accordingly, it is desirable to provide a synthetic fabric vascular graft suitable for a wide variety of dimensions and diameters providing the benefits of woven grafts, but do not tend to unravel when cut and which do not require crimping and will be self-supporting and maintain an open lumen,

SUMMARY OF THE INVENTION

Generally speaking, in accordance with the invention, a ravel-resistant, self-supporting woven synthetic vascular graft having improved kink resistance and incorporating fusible components into the weave are provided. A plurality of multifilament warp yarns and filling yarn are woven in tubular form and include a fusible component to prevent unravelling. The filling yarn may include a stiffening component to prevent collapse and provide a tubular graft of increased radial resiliency. The warp yarns may be the same as one another or include flat and texturized multifilament yarns. A filling of stiffer monofilament yarn and fusible components provide radial burst strength, dimensional stability and radial rigidity with resiliency to maintain the lumen of the tubular structure open and provide a sufficient degree of ravel resistance. The graft surface may be smooth or a single or a double velour.

In a preferred embodiment of the invention, the fusible component of the filling is a yarn formed from bicomponent fiber having a polyester core surrounded by a low melting temperature polymer sheath designed to bond to neighboring yarns to form a solid bond after exposure to heat. In another preferred embodiment, the ravel-resistant, self-supporting woven vascular graft has an exterior surface similar to a velour. The inner surface is provided with a fine, low profile woven surface to promote smooth, thin pseudointima formation. The loops on the exterior surface are formed of multifilament warp yarns which provide the necessary texture cover for tissue adhesion and ingrowth. The density of the multifilament warp yarns also controls blood porosity.

The woven grafts prepared in accordance with the invention are particularly well suited to 2–6 mm diameter peripheral vascular prosthesis, but are suitable for larger dimensions up to about 40 mm as well. Kink resistance is provided without the necessity to crimp the vascular graft.

Accordingly, it is an object of the invention to provide an improved woven synthetic vascular graft.

Another object of the invention is to provide a self-supporting woven synthetic vascular graft which is ravel-resistant.

A further object of the invention is to provide synthetic woven vascular graft which resists kinking without the need to crimp the graft.

A further object of the invention is to provide a woven synthetic fabric vascular graft which is suitable for peripheral use in small diameters of 6 mm or less.

Still another object of the invention is to provide a small diameter of woven synthetic fabric vascular graft which resists kinking and provides a desirable amount of longitudinal stretch without crimping.

Still a further object of the invention is to provide a ravel-resistant woven synthetic fabric vascular graft which includes an outer velour surface to promote tissue ingrowth.

Yet another object of the invention is to provide a self-supporting woven synthetic vascular graft having a fine, low profile woven surface to promote smooth, thin pseudointima formation.

Yet a further object of the invention is to provide a ravel-resistant woven synthetic fabric single-velour vascular graft having improved kink resistance without crimping.

Another object of the invention is to provide a method of preparing an improved ravel-resistant woven synthetic fabric vascular graft in accordance with the invention.

Still other objects and advantages of the invention will in part be obvious and will in part be apparent from the specification.

The invention accordingly comprises the several steps and the relation of one or more of such steps with respect to each of the others, the apparatus embodying features of construction, combination and arrangement of parts which are adapted to effect such steps, and the product which possesses the characteristics, properties, and relation of constituents (components), all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawing(s), in which:

FIG. 1 is a weaving diagram of a ravel-resistant woven synthetic fabric vascular graft prepared in accordance with a preferred embodiment of the invention;

FIG. 2 is a cross-sectional view in schematic in the warp direction a finished graft surface showing the interlacing ends and of the filling yarn of a graft fabric having the weave pattern of FIG. 1;

FIG. 3 is a cross-sectional view of an enhanced filling yarn of the graft substrate of FIG.

FIG. 4 is a cross-sectional view of a staple bicomponent fiber of the fusible component of the filling yarn of FIG. 3;

FIG. 5 is a perspective view of a tubular ravel-resistant woven single-velour vascular graft prepared in accordance with the invention; and FIG. 6 is a perspective view of a bifurcated ravel-resistant woven single-velour vascular graft prepared in accordance with the invention.

DESCRIPTION OF THE PREFERRED EMBODIMENTS

The woven synthetic vascular grafts prepared in accordance with the invention are applicable to a wide range of diameters, including the small 2 to 6 mm diameter range suitable for peripheral use as well as dimensions up to about 40 mm. Accordingly, the grafts may be woven having inside diameters which range from about 2 to about 40 mm are resistant to unravelling and are self-supporting and resist kinking without being crimped.

In a preferred embodiment of the invention, the woven graft has a diameter of 6 mm or less. In another preferred embodiment the woven graft has a exterior surface with loops and a smooth interior surface. The grafts are ravel-resistant, and are self-supporting and resistant to kinking without crimping the fabric surface. The grafts possess ravel-resistance imparted by heat setting warp and/or filling yarns which include fusible bicomponent staple fibers having a polyester resin core and low melting copolyester or polyethylene sheath. During heat setting the fusible resin sheath in the yarns in the woven fabric bond to each interlacing yarn in the weave. The fusible yarn is composed of Celbond Type K54 bicomponent staple fibers from Hoechst Celanese. The staple fibers are available 1½ to 3 inches in length and 2 to 15 denier. The yarns utilized are compatible biologically.

The stiffening component in the filling yarns may be a monofilament. Selection will vary depending on the desired characteristic of the tubular graft. However, the stiffening component must be sufficiently stiff to impart dimensional stability and radial rigidity to the tube without crimping. The stiffening component should have the following minimum physical properties:

Tenacity ≥ 3 grams per denier Diameter: >2< 10 mils (53,000 psi)
Initial Modulus ≥ 50 grams/denier (800,000 psi)
$EI \geq 3.9 \times 10^{-8}$ lb. in.$^2$ Where EI is the calculated bending stiffness, E is the modulus of elasticity, I is the moment of inertia $$I = \frac{\pi r^4}{64}$$

The diameter m can vary depending on desired characteristics, but will typically be in the range of 2 to 10 mils.

The grafts possess longitudinal elasticity imparted by heat setting when the graft is longitudinally compressed. This compresses the warp yarns to impart the stretch without having to crimp the fabric surface.

Preferably, the majority of the yarns utilized in the woven graft are polyethylene terephthalate, such as Dacron polyester available from du Pont or polyester available from Teijin, Hoechst-Celanese and Toray Industries. The graft substrate is formed by weaving a plurality of warp ends of multifilament yarns with a combined filling yarn of fusible yarn and stiffer monofilament yarn which have been plied or wound together prior to weaving. The woven fabric is heat set to bond the bicomponent fibers to orthogonal warp yarns to provide longitudinal compliance which maintains integrity of the graft. The bonding of the low melting sheath of the bicomponent staple fibers to the interlacing warp yarns provide ravel-resistance. The plurality of bond sites allows the tubular graft to be cut at any angle and maintain ravel-resistance.

The monofilament polyester utilized as a stiffening component in the Example which follows is a 5 mil polyethylene terephthalate yarn. The yarn has the following physical properties:

Diameter: .005(5 mils or 0.127 mm)
Tenacity: 6.2 grams per denier (110,000 psi)

Initial Modulus = 112 grams per denier (1,980,000 psi)

$I$ (moment of inertia): $\frac{\pi r^4}{64}$

Calculated Bending Stiffness = $E \times I$
$EI = 3.8 \times 10^{-6}$ lb. in$^2$.

The fusible fiber, Celbond, is composed of a polyester core and a copolyester or polyethylene sheath. It is the sheath of the fiber that provides the adhesion. The sheath resins available melt in the 110°–200° C. range, whereas the core resin melts at about 260° C. The fiber can either be spun into a yarn itself and combined with the monofilament or it can be combined directly with the monofilament using the core spinning process. This produces a yarn with a monofilament core with the Celbond fibers wrapped about it forming a sheath.

The fusible component may be a fiber composed entirely of fusible resin, where the entire fiber would melt, not just the sheath. It is also possible to use multifilament yarns, whether they are bicomponent or single component, in place of staple yarn. The low temperature melting resin may also be applied directly to the outside of the monofilament component of the filling yarns through coextrusion or post coating processes. This would replace the use of the celbond fiber in the Example.

During the heat setting process, when the tubing is being formed into a tubular vascular graft, the bicomponent celbond fiber fuses to the orthogonal warp yarns. This means that the filling and warp yarns are fused together at every interlace. This fusing allows the finished graft to be cut at any angle without the yarns shifting, separating, or ravelling.

Stretch is built into the graft by weaving the fabric with 25 to 50% fewer picks per inch than in the finished graft. During the finishing process, the tubing is compressed longitudinally 25 to 50% while on a forming mandrel, and heat set. Heat setting in this manner causes the warp yarns to crimp and buckle, which builds stretch into them. It is this stretch that allows the finished grafts to be flexible longitudinally without the need to crimp the surface of the graft.

The stiffer monofilament component of the filling yarn can be any compatible yarn, such as polyethylene terephthalate, polyurethane, polytetrafluoroethylene or silicone. It provides mechanical strength, dimensional stability and radial rigidity which maintains an open lumen for normal blood flow and provides the necessary burst strength. The multifilament warp yarns provide the necessary texture and cover for tissue adhesion and ingrowth on the outer surface and assist in controlling porosity of the graft. The velour prepared loops are of multifilament warp pile yarns on the outer surface only. In the preferred single velour construction, the external velour surface promotes tissue adhesion and ingrowth. The inner surface has a fine, low profile which promotes smooth, thin neointima formation.

The particular selection of multifilament warp yarns together with the stiffer combined fusible staple yarn and monofilament filling yarns provide a graft having improved kink resistance over a wide range of diameters. Thus, smaller bending radii can be achieved without occluding.

FIG. 1 illustrates the weaving pattern of a woven vascular graft substrate 11 prepared in accordance with a preferred embodiment of the invention. Substrate 11 is woven from a plurality of warp ends 12 and filling yarn 13. FIG. 2 is a schematic of substrate 11 in cross-section with a smooth interior surface 14 and a velour exterior surface 16 having loops 17 of multifilament warp yarns 19 which stand away from the surface of the graft.

Referring to FIG. 1, warp ends 12 include ground warp ends of multifilament yarn 18. In the illustrated embodiment multifilament yarn 18 is a one ply fifty denier untexturized unshrunk (flat) polyethylene terephthalate (Teijin) yarn (1/50/48) (single ply/50 denier/48 filaments) with a 5z twist. The loop or pile component 19 of warp yarns 12 is a multifilament yarn which alternates with each end of ground warp ends 18. In substrate 11, multifilament warp yarn 19 is a texturized 2/50/48 (2 ply/50 denier/48 filamament) with 1.5s twist polyethylene terephthalate (Teijin) yarn.

Filling yarn 13 is a combination of a monofilament yarn component 21 combined with a fusible staple yarn component 22 as shown in detail in the cross-section of FIG. 3. Fusible yarn 22 which is formed from bicomponent staple fibers 25 having a polyester core 23 with a low melting temperature sheath of a copolyester resin 24 surrounding core 23 as shown in the enlarged cross-sectional view of a single fiber 25 in FIG. 4. Fusible yarn 22 is 40 cc (English Cotton Count) Celbond Type K54, formed from 2 denier/2" staple fibers with a twist multiplier of 4 (about 25 turns per inch) having a sheath melting point of 110° C. The components are plied together with or without twisting prior to weaving.

FIG. 5 is a perspective view of a tubular graft 31 prepared in accordance with the invention. Graft 31 has a smooth inner surface 32 and external raised fabric velour surface 33 having a multiplicity of outwardly extending loops 34. Similarly, FIG. 6 illustrates a bifurcated graft 41 having a main body segment 42 and two legs 43 and 44. Legs 43 and 44 are joined to main body 42 at a crotch 46 which is generally reinforced by a row of stitches 47 to maintain as tight an initial porosity of the graft as possible. Graft 41 has a smooth interior surface 48 and an external surface 49 having loops 51. As is evident from the weaving pattern of FIG. 1, loops 34 and 51 of grafts 31 and 41, respectively are formed from multifilament warp yarns. In substrate 11 warp yarns 19 are texturized unshrunk polyester yarns.

After weaving substrate 11 in the pattern as shown in FIG. 1, tubular grafts 31 and 41 are cut, then scoured and washed in a hot bath which results in about 10 to 30 percent shrinkage or relaxation. The tubes are then subjected to a first heat setting step by placing on a specific straight size mandrel in a longitudinally stretched condition and placed in a convection oven at 175° C. for about 20 minutes to give the graft a rounded condition and fuse the Celbond yarns to the yarns in contact with it. The grafts are then subjected to a second heat setting step on the same size mandrel, but compressed longitudinally about 25 to 50 percent. This second heat setting step in the compressed state builds in longitudinal stretch and structural integrity and kink resistance without the need to crimp the graft wall. The grafts can also be heat set in a non-straight condition to create shaped grafts, such as an aortic arch, which will not have to be bent or shaped by the surgeon during implantation.

As shown in FIGS. 5 and 6, tubular woven vascular grafts and 41 prepared in accordance with the invention are not crimped in order to maintain an open lumen. This is due to inclusion of the relatively stiffer monofilament component 21 in filling yarns 13 and fusing of bicomponent yarn 25 to orthogonal warp yarns 12.

The specifications of the yarns utilized and substrate 11 are set forth in the following Example. This Example is presented for purposes of illustration and is not intended in a limiting sense.

EXAMPLE

Seven sizes of tubular grafts were woven with the following yarns in the pattern of FIG. 1.

TUBULAR WEAVE CONSTRUCTION:

Ground weave for lattice structure-plain:
Flat weave for loop or pile surface:
Warp crowfoot (floats on outside surfaces, See FIG. 2) alternates on every other end (See FIG. 1)
YARN CONSTRUCTION:

Warp Ground - 1/50/48 (5z) Teijin Polyester.
Warp Pile - 2/50/48 (1.5s) Texturized Unshrunk Polyester Teijin.
Filling - 5 mil PET Monofilament wound together with 40 cc Celbond K-54 polyester.
Density Description SLEY: 320 ends per inch (40 dents per inch × 8 ends per dent)
PICKS: 44 picks per inch layer (88 total in tubular form) inserted, 46 relaxed (off loom)
TUBE DESCRIPTION GREIGE INSIDE DIAMETERS: 4.3, 5.3, 6.3, 7.3, 8.3, 9.3 & 10.3 mm
FINISHED INSIDE DIAMETER: 4, 5, 6, 7, 8, 9 & 10 mm The velour was formed by weaving every other warp end in a crowfoot pattern, which allows the warp yarn which formed the loop to float over three picks and under one pick. The remaining adjacent ends form a plain weave.

After weaving, the single velour graft materials of Example 1 were cut, scoured at 80° C. in water and detergent bath, and thoroughly rinsed, dried, and then rinsed in a hot water bath at about 70° C. to remove trace chemicals and dried. The graft tubes shrank about 10–20 percent in length.

The tubes were then placed on an appropriately sized straight mandrels in a longitudinally stretched condition and heat set at 175° C. for 20 minutes in a convection oven to give a round shape and fuse the Celbond yarns. The tubes were then compressed longitudinally about 30 to 40 percent of their length and heat set again on the same size mandrel at 175° C. for 20 minutes in a convection oven. Preferably, the compression is about 25–50% in length.

The porosity of the grafts were estimated to be about 1000 ml/min/cm$^2$.

The longitudinal compliance of a tubular vascular graft is a relative measurement of the ability of the graft to elongate at a given force and is expressed as the percent elongation per kilogram force. The grafts prepared in the Example were stretched about 30% in length from 0 to 1 when tension was increased Kg. This allows the graft to bend easily without kinking. The fusible component did not adversely affect the feel or flexibility compared to conventional woven grafts.

After fusing in the heat setting steps, the yarns could not be unravelled from the tubing ends, even after cutting the graft ends at angles.

The characteristics and properties of the grafts woven in accordance with the invention can be varied as desired by selection and combination of the starting warp and filling yarns and the weaving pattern. In the illustrated examples, the warp ground yarns are multifilament untexturized unshrunk (or flat) polyester yarn, but could be preshrunk or unshrunk in untexturized form or a combination of yarns alternating in desired patterns. The preferred warp yarn forming the pile is a multifilament texturized polyester, but could also be preshrunk or unshrunk in texturized or untexturized form. The sole limiting feature is that there be sufficient multifilament yarns considering the desired end results. The filling yarn is a composite fusible bicomponent yarn combined with a monofilament polyethylene terephthalate yarn.

It will thus be seen that the objects set forth above among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A ravel-resistant and self-supporting tubular synthetic fabric vascular graft resistant to kinking, comprising:

a plurality of warp yarns woven with at least one filling yarn to form a weave;

the filling yarn including a stiffening component in the weave which is heat set in a rounded condition to render the tubular graft self supporting; and the weave including a low melting temperature fusible component having a melting temperature lower than the other yarns to bond to adjacent yarns when heat set.

2. The woven vascular graft of claim 1, further including a low melting temperature fusible component in the filling yarn.

3. The woven vascular graft of claim 1, wherein the low melting fusible component is a bicomponent fiber having a high melting temperature core and a low melting temperature polymer sheath.

4. The woven vascular graft of claim 1, wherein the warp yarns include multifilament textile yarns.

5. The woven vascular graft of claim 4, wherein the multifilament yarns are polyethylene terephthalate.

6. The woven vascular graft of claim 5, wherein the multifilament polyethylene terephthalate warp yarns are unshrunk untexturized yarns.

7. The woven vascular graft of claim 1, wherein the stiffening component is a monofilament yarn of polyethylene terephthalate.

8. The woven vascular graft of claim 1, wherein the monofilament yarn is a 5 mil yarn.

9. The woven vascular graft of claim 8, wherein the vascular graft is a tube with a single outside velour surface and a smooth interior surface, the velour surface formed from warp pile yarns of texturized multifilament yarn.

10. The woven vascular graft of claim 1, wherein the graft has at least one velour surface of a plurality of warp pile yarns of multifilament yarns.

11. The woven vascular graft of claim 10, wherein the warp pile yarns alternate between each said warp yarn.

12. The woven vascular graft of claim 10, wherein the multifilament warp pile yarns are polyethylene terephthalate.

13. The woven vascular graft of claim 12, wherein the warp pile yarn is texturized polyethylene terephthalate.

14. The woven vascular graft of claim 10, wherein the vascular graft is a tube with a single outside velour surface and a smooth interior surface, the velour surface formed from warp pile yarns of preshrunk texturized multifilament yarn.

15. The woven vascular graft of claim 1, wherein the graft has been heat set to bond the fusible components to adjacent yarns.

16. The woven vascular graft of claim 1, wherein said weave is set in a longitudinally-compressed state to provide said graft with longitudinal compliance and kink resistance.

17. The woven vascular graft of claim 1, wherein said stiffening component is present in each pick of the weave.

18. The woven vascular graft of claim 1, wherein said weave further comprises a plurality of pile yarns for providing a velour surface on at least one side of said weave.

19. A self-supporting singular velour woven synthetic fabric vascular graft, comprising:

a plurality of warp ground yarns and a plurality of warp pile yarns woven together with at least one filling yarn to form a weave;

the filling yarn including a stiffening component in the weave which is heat set in a rounded condition to render the graft self-supporting; and the weave including a low melting temperature fusible component which melts at a lower temperature than the other yarn to bond to adjacent yarn when heat set.

20. The woven vascular graft of claim 19, wherein the filling yarn includes a yarn of low melting fusible fibers wound together with the stiffening component.

21. The woven vascular graft of claim 19, wherein the low melting temperature fusible component is a yarn of bicomponent fibers having a core surrounded by a low melting temperature polymer sheath wound together with a monofilament yarn.

22. The woven vascular graft of claim 19, wherein the warp pile yarns alternate with the warp ground yarns.

23. The woven vascular graft of claim 22, wherein the vascular graft is a tube with a single outside velour surface and a smooth interior surface, the velour surface formed from warp pile yarn of texturized multifilament yarn.

24. The woven vascular graft of claim 22, wherein the warp ground yarn includes unshrunk untexturized yarn.

25. The woven vascular graft of claim 19, wherein the graft has been heated sufficiently to bond the fusible component to adjacent yarns.

26. The self-supporting single velour woven synthetic vascular graft of claim 19, wherein said weave is set in a longitudinally-compressed state to provide said graft with longitudinal compliance and kink resistance.

27. The self-supporting single velour woven synthetic vascular graft of claim 19, wherein said stiffening component is present in each pick of the weave.

* * * * *

UNITED STATES PATENT AND TRADEMARK OFFICE
CERTIFICATE OF CORRECTION

PATENT NO. : 5,509,931
DATED : April 23, 1996
INVENTOR(S) : Schmitt

It is certified that error appears in the above-indentified patent and that said Letters Patent is hereby corrected as shown below:

| | |
|---|---|
| At. Col. 2, line 62, | "grafts described above," should be --grafts described above.--; |
| At Col. 2, line 67, | "an open lumen," should be --an open lumen.--; |
| At Col. 4, line 24, | "an enhanced filling" should be --an enlarged filling--; |
| At Col. 5, line 12, | "The diameter m" should be --The diameter--; |
| At Col. 5, line 63, | "the celbond" should be --the Celbond--; |
| At Col. 5, lines 66-67, | "the bicomponent celbond" should be --the bicomponent Celbond--; |
| At Col. 7, lines 26-27, | "grafts and 41" should be --grafts 31 and 41--; |
| At Col. 7, line 52, | "Density Description" should be -- DENSITY DESCRIPTION:--; and |

UNITED STATES PATENT AND TRADEMARK OFFICE
CERTIFICATE OF CORRECTION

PATENT NO. : 5,509,931
DATED : April 23, 1996
INVENTOR(S) : Schmitt

It is certified that error appears in the above-indentified patent and that said Letters Patent is hereby corrected as shown below:

At Col. 7, line 54,          "per inch layer" should be --per inch per layer--.

Signed and Sealed this

Sixth Day of August, 1996

Attest:

BRUCE LEHMAN

Attesting Officer         Commissioner of Patents and Trademarks